United States Patent [19]

Sommer

[11] Patent Number: 5,569,608
[45] Date of Patent: Oct. 29, 1996

[54] QUANTITATIVE DETECTION OF ANALYTES ON IMMUNOCHROMATOGRAPHIC STRIPS

[75] Inventor: Ronald G. Sommer, Elkhart, Ind.

[73] Assignee: Bayer Corporation, Elkhart, Ind.

[21] Appl. No.: 380,119

[22] Filed: Jan. 30, 1995

[51] Int. Cl.$^6$ .................................................. G01N 33/544
[52] U.S. Cl. ..................... 436/518; 436/523; 436/525; 436/513; 436/514; 436/810; 435/810; 435/805; 435/970; 422/56
[58] Field of Search ................................ 435/7.92, 169, 435/810, 805, 970; 436/523, 169, 525, 514, 810; 422/63, 56; 23/230 B

[56] References Cited

U.S. PATENT DOCUMENTS

| | | | |
|---|---|---|---|
| 4,168,146 | 9/1979 | Grubb et al. | 424/230 B |
| 4,313,734 | 2/1982 | Leuvering | 23/230 |
| 4,376,110 | 3/1983 | David et al. | 436/513 |
| 4,446,232 | 5/1984 | Liotta | 435/7 |
| 4,772,561 | 9/1988 | Genshaw | 436/169 |
| 4,833,088 | 5/1989 | DeSimone et al. | 435/289 |
| 4,855,109 | 8/1989 | Muraishi et al. | 422/63 |
| 4,859,612 | 8/1989 | Cole et al. | 436/523 |
| 4,868,108 | 9/1989 | Bahar et al. | 435/7 |
| 4,943,522 | 7/1990 | Eisinger et al. | 435/7 |
| 5,110,550 | 5/1992 | Schlipfenbacher et al. | 422/56 |
| 5,120,643 | 6/1992 | Ching et al. | 435/7.92 |
| 5,141,850 | 8/1992 | Cole et al. | 436/525 |
| 5,308,775 | 5/1994 | Donovan et al. | 436/518 |

FOREIGN PATENT DOCUMENTS 2204398  11/1988  United Kingdom.

OTHER PUBLICATIONS

Butler, John E., Immunochemistry of Solid–Phase Immunoassay, 1991, p. 144.

*Primary Examiner*—James C. Housel
*Assistant Examiner*—Bao-Thuy L. Nguyen
*Attorney, Agent, or Firm*—Jerome L. Jeffers

[57] ABSTRACT

A method for determining the concentration of analyte in a test fluid by immunochromatography techniques which involves quantitatively determining the signals from captured analyte/labeled binding partner complex by an instrument, e.g. reflectance spectrometer. In a preferred embodiment, a reflectance reading is determined for the captured complex and uncomplexed labeled binding partner which is captured in a separate zone of the immunochromatographic strip and the ratio of these reflectances is used to provide additional quantitation to the assay method.

16 Claims, 5 Drawing Sheets

QUANTITATIVE DETECTION OF ANALYTES ON IMMUNOCHROMATOGRAPHIC STRIPS

BACKGROUND OF THE INVENTION

Immunochromatographic strip formats are increasingly popular for qualitative and semi-quantitative assays which use visual detection schemes. This type of immunoassay involves the application of a liquid test sample suspected of containing an analyte to be detected to an application zone of an immunochromatographic test strip. The strip is comprised of a matrix material through which the test fluid and analyte suspended or dissolved therein can flow by capillarity from the application zone to a detection zone where a visible signal, or absence of such, reveals the presence of the analyte. Typically, the strip will include means for immunospecifically binding the analyte to be detected with its specific binding partner which bears a detectable label. In one such scheme; as disclosed in U.S. Pat. No. 04,446,232; the strip contains an enzyme labeled, mobile binding partner for the analyte which is in a zone downstream from the sample application zone. If analyte is present in the test sample, it will combine with its labeled binding partner to form a complex which will flow along the strip to a detection zone which contains a substrate for the enzyme label capable of providing a colored response in the presence of the enzyme label. The strip contains a zone in which analyte is immobilized, so that labeled binding partner which does not combine with analyte, due to absence of analyte in the sample, will be captured and thereby inhibited from reaching the detection zone. There have been published various modifications of this technique, all of which involve some competitive specific binding system in which the presence or absence of analyte in the test sample is determined by the detection or lack thereof of labeled binding partner in the detection zone. In U.S. Pat. No. 4,868,108 there is disclosed a similar scheme with the addition of an immobilized capture reagent for the enzyme labeled binding partner in the detection zone to concentrate the enzyme label and enhance its ability to react with the enzyme substrate and thereby render the assay more sensitive.

Not all of the schemes for immunochromatography rely on an enzyme labeled binding partner/enzyme substrate as providing the signal for detection of the analyte. In U.S. Pat. No. 4,806,311 there is disclosed a multizone test device for the specific binding assay determination of an analyte and an immobilized binding partner therefore together with a detection zone for receiving labeled reagent which migrates thereto from the reagent zone. The detection zone contains an immobilized form of a binding substance for the labeled reagent. The labeled reagent bears a detectable chemical group having a detectable physical property which is detectable on the basis of its own physical properties, so that it does not require a chemical reaction with another substance. Exemplary of such groups are colored species fluorescers, phosphorescent molecules, radioisotopes and electroactive moieties.

U.S. Pat. No. 4,313,734 describes the use of gold sols as labels for antibodies which are detectable without a chemical change.

Immunochromatographic strip formats provide a viable system for the determination of various analytes (whether they be antigens or antibodies) but suffer from the limitation that they yield results which are at best semi-quantitative when, for some analytes, a quantitative answer is required. Accordingly, it would be desirable and it is an object of the present invention to provide a means for quantifying the results of analyses carried out by the use of immunochromatographic strip formats.

SUMMARY OF THE INVENTION

The present invention involves an improvement to a method for determining an analyte in a test fluid which involves applying the test fluid to an immunochromatographic matrix which allows the test fluid; and the analyte, if present; to flow through the matrix by capillarity and which matrix contains a labeled binding partner for the analyte. The matrix, which is normally in the form of a test strip, also contains at least one detection zone in which the presence or absence of the analyte is determined by detecting the label carried by the specific binding partner. The improvement involves determining the concentration of the label using an instrument having a detector capable of determining its concentration in the detection zone(s).

In a preferred embodiment of the present invention there is provided a test strip comprising a strip having a first region which contains mobile specific binding partner for the analyte which bears a detectable label and can react with the analyte to form an analyte/labeled binding partner complex and at least one second region which contains an immobilized analyte or analog thereof. The term analog as used herein refers to any substance capable of being bound by the active site of the specific binding partner.

The strip as described above is developed by applying the test fluid sample suspected of containing the analyte thereto thereby allowing it to contact the mobile, labeled specific binding partner for the analyte whereby analyte present in the fluid test sample binds to the labeled specific binding partner to form the complex; leaving excess, unreacted labeled binding partner free to further react whereby the fluid test sample carries the analyte/labeled binding partner conjugate and unreacted labeled binding partner along the strip by capillarity to the second region containing the immobilized analyte or analog thereof in which unreacted labeled binding partner is bound to the immobilized analyte in inverse relationship to the concentration of analyte in the fluid test sample.

The developed strip is read on an instrument having a detector capable of measuring the signal from the detectable label to determine the signal from the labeled binding partner in the second region. The concentration of the analyte in the fluid test sample is determined by comparing the signal from the detectable label with determinations made in a similar manner using fluid test samples containing known concentrations of analyte.

The sensitivity of the determination can be enhanced by providing a strip with a third region which region contains means for immobilizing the complex formed between the analyte and the labeled binding partner therefor. For example, if the labeled binding partner in a labeled mouse antibody (IgG) is used, the complex of this mouse antibody and the analyte can be captured in a zone of immobilized goat anti-mouse IgG. By measuring the signal from the detectable label immobilized in this third region and determining the ratio of the signal labeled binding partner in the second region to that in the third region, inaccuracies caused by uneven deposition of labeled conjugate and/or non-uniform fluid flow through the matrix can be corrected.

BRIEF DESCRIPTION OF THE INVENTION

FIG, 7 represents the reflectance values obtained with a fluid test sample containing both HSA and IgG.

DETAILED DESCRIPTION OF THE INVENTION

The present invention is practiced by first providing a test matrix through which the fluid test sample can flow by capillarity. Typically, the matrix will be in the form of a strip through which the test fluid flows horizontally although the matrix could be set up in layers through which the test fluid could flow vertically from top to bottom or vice-versa. The following discussion will focus on the strip format.

The strip can be prepared from any matrix material through which the test fluid and an analyte contained therein can flow by capillarity. The matrix can be of a material which is capable of non-bibulous lateral flow. This type of flow is described in U.S. Pat. No. 4,943,522 as liquid flow in which all of the dissolved or dispersed components of the liquid are carried through the matrix at substantially equal rates and with relatively unimpaired flow, as opposed to preferential retention of one or more components as would be the case if the matrix material were capable of adsorbing or imbibing one or more of the components. An example of such a matrix material is the high density or ultra high molecular weight polyethylene sheet material from Porex Technologies of Fairburn, Ga. Equally suitable for use as the matrix material from which the chromatographic strips can be fabricated are bibulous materials such as paper, nitrocellulose and nylon.

Various immunochromatographic strip formats are suitable for use in conjunction with the present invention. A particularly suitable format is that which is disclosed in U.S. Pat. No. 4,446,232 wherein there is described a device for the determination of the presence of antigens, which device comprises a strip of matrix material having a first zone in which there are provided immobilized analyte and enzyme linked antibodies specific to the analyte to be determined. The labeled antibodies can flow to a second zone when reacted with analyte introduced into the first zone but will not so flow in the absence of analyte in the test fluid due to being bound in the first zone by interaction with the immobilized analyte. The analyte is typically an antigen, although the format can be designed to detect the presence of antibodies as analyte. Modifications to this format are disclosed in U.S. Pat. No. 4,868,108. In another modification, the enzyme substrate is disposed in the region of a second, immobilized antibody to thereby capture the complex formed between the enzyme labeled antibody and the analyte. This sort of format is particularly suitable for adaptation to the present invention, although any physically detectable signal may be used since the present invention need not be limited to the interaction of an enzyme and its substrate to provide the detectable signal. Thus, by immobilizing the conjugate in a discrete detection zone located downstream on the strip from the zone in which the labeled binding partner for the analyte is bound, there are provided two zones from which the physically detectable property of the detectable label can be measured to determine its concentration. By measuring the signal from the physically detectable property of the detectable label in the second zone containing the immobilized analyte as the capture means and the signal from the physically detectable property of the label in the third zone, in which the immobilized antibody against the labeled binding partner is the capture means, and determining the ratio of these signals, the accuracy of the test for analyte concentration can be increased. The accuracy is increased because this technique corrects for inaccuracies in labeled conjugate deposition and/or non-uniform fluid flow through the matrix. More particularly, since the aforementioned inaccuracies of labeled conjugate deposition and non-uniform fluid flow are usually of small but significant magnitude, they do not disturb substantially the binding equilibrium. Therefore, the ratio of the signals in the two binding zones is a more accurate measure of the analyte concentration than is the signal in either zone by itself.

In a preferred embodiment of the present invention, there is provided a reflectance spectrometer with means for moving the strip or detector relative to each other such as a specimen table on which the strip is placed which can be moved laterally under the read head of the detector. In the case of the detectable physical property being reflectance of light at a predetermined wavelength, the detector is a spectrometer. This technique will assist in providing accurate quantitation for regions of the strip which may not have been precisely located with respect to the detection means of the spectrometer. More specifically, the location of the strip relative to the detector can be under microprocessor control, so that the reflectance of any desired region can be determined.

The method of practicing the present invention is more fully illustrated by the following examples:

EXAMPLE I

Quantitation of HSA in a Single Blocking Band Format

Figure 1:
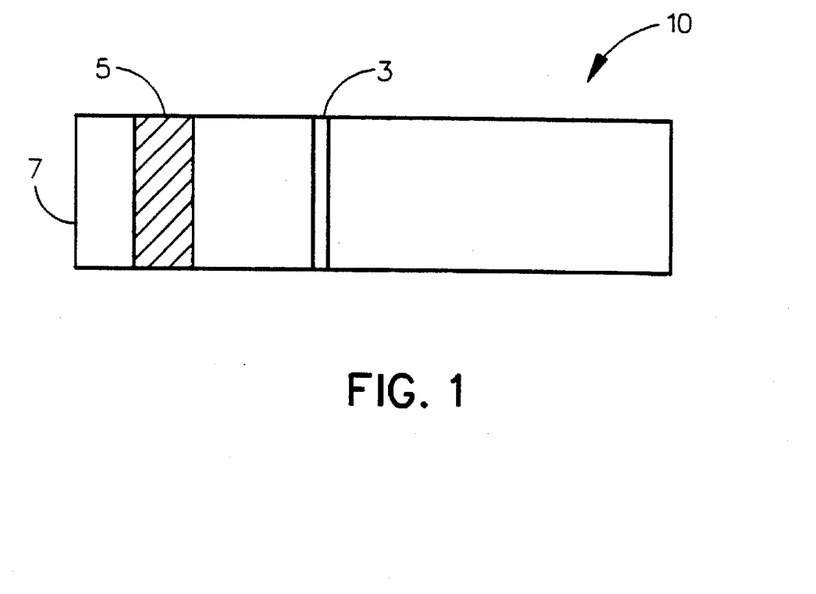
FIG. 1 illustrates an immunochromatographic strip suitable for use in the present invention.

An immunochromatographic strip containing a blocking band of immobilized HSA and a broad area of anti-HSA:gold sol conjugate in an Immunodyne™ nylon membrane was prepared. This strip is illustrated by FIG. 1 wherein the strip 10 contains blocking band 3, preceded by the anti-HSA:gold sol containing region 5 and the sample application area 7. These strips were prepared as follows:

A 4.2×12.6 centimeter piece of Immunodyne® membrane was placed on a Comag Thin Layer Chromatography (TLC) stripping apparatus with the long side parallel to the base and offset 1 cm up from the O position of the Y axis. Next, a solution of human serum albumin (HSA) with a concentration of 10 mg/mL was prepared in phosphate buffered saline (PBS; 0.137M sodium chloride, 0.0027M potassium chloride, 0.010M potassium phosphate, pH 7.4). At a Y position of 3.5 cm a 6 cm long band of the 10 mg/mL HSA solution was stripped using the following settings of the TLC stripper:

(a) plate=90, (b) band=60, (c) sec/μL+6, (d) volume=6 µL.

This gave a band 6 cm long and approximately 1 mm wide. The stripping density was therefore 10 µL/cm$^2$ with a density of 100 µg of HSA/cm$^2$.

After 3 minutes the membrane was removed from the TLC stripper and placed in a flat plastic tray containing 0.5% casein (Hammerstein from Schlesinger) in phosphate buffered saline (pH 7.4 from Sigma) and gently rocked on an orbital shaker for 30 minutes.

At this point a wash buffer was prepared as 0.02% sodium azide, 0.02% Tween 20 and 0.1% PEG 20 in PBS. The membrane was removed from the casein blocking solution and was twice washed with 25 mL of wash buffer for 30 minutes with gentle rocking on an orbital buffer whereupon the membrane was removed from the wash buffer and allowed to dry overnight at room temperature.

Gold sol was prepared by adding 2.0 mL of a 10 mg/mL solution of acid gold chloride monohydrate (HCl$_4$Au.H$_2$O) to a refluxing 100° C. solution of tri-sodium citrate (0.00155M). The refluxing was continued for 30 minutes and then cooled and filtered through a 0.2 µM filter. Antibody-gold sol conjugate (Ab:gold sol) was prepared by adding 240 µg of monoclonal antibody against human serum albumin and 50 µL of 0.1M potassium carbonate to 10 mL of the gold sol solution prepared as described above and the mixture was allowed to stir vigorously for 15 minutes, whereupon 0.5 mL of 1% (w/v) PEG-20 was added followed by another 10 minutes of vigorous stirring. At this point, 1.0 mL of 10% bovine serum albumin (BSA) in water was added and the mixture stirred vigorously for 10 minutes. The Ab:gold sol was isolated by centrifugation at 14,500×g for 30 minutes all 20° C. and then washed 10 times by suspending it in a wash buffer (1% BSA, 0.05% PEG-20, 2 mM sodium borate, pH=9.0) and isolated by centrifugation as described above. After the final centrifugation, the Ab:gold sol was suspended in 1.0 mL of wash buffer and stored at 4° C.

The dried membrane described above was again placed on the TLC stripper at an offset of 1 cm in the Y direction as before. A mixture of 40 µL of Ab:gold sol, 20 µL of 4% casein and 20 µL of 1% Methocel (K4M)+0.6% polyvinyl alcohol (PVA) was prepared and seven adjacent bands were stripped as before between the Y positions of 2.3 and 2.9 cm. The strip was allowed to dry at room temperature and slit into 0.5 cm wide strips before use.

A medium specific gravity (S.G.+1.017) pool of urine was filtered through an ultrafiltration membrane which held back proteins larger than 30,000 daltons. The filtrate was used to prepare HSA solutions of various known concentrations by spiking them with an HSA solution of known concentration.

The strips were developed by suspending them vertically in a solution of HSA spiked urine filtrate to a depth of approximately 0.5 cm (on the end of the strip containing the Ab:gold sol conjugate bands) and allowing 5–10 minutes for the liquid to reach the top of the strip. These strips were allowed to air dry at room temperature and then mounted on plastic trycite handle material and analyzed.

The strips were developed with samples of an ultrafiltrate of medium specific gravity urine containing 0, 1, 2, 3 and 5 mg/dL HSA. The strips from each sample concentration were read by measuring the reflectance at 557 nm on a CT100 reflectance photometer with scanning of the strip being simulated by cutting one millimeter off its end between measurements.

More particularly after the strips were developed with sample fluid and allowed to air dry at room temperature, they were mounted on plastic handle material using double sided adhesive. The plastic/membrane laminate was trimmed to 7 mm (toward the sample application end) from the HSA band 3 (FIG. 1) which was visible due to the bound Ab:gold sol. The strip was then placed on the read table of a CT100 reflectance photometer with the strip pushed to the end stop. In this position the read area of the 10$^{th}$ pad position is 2.5 mm from the end of the strip. The reflectance of the 10$^{th}$ pad position was then measured after which 1 mm was cut from the end of the strip and the strip pushed to the end of the read table. The 10$^{th}$ pad position was again read and this process was repeated until the end of the plastic and membrane laminate corresponded to a point which was 3 mm past the HSA band. This technique was used to move the read head (detector) in relation to the read zone (HSA band) since software was not available to perform this task. With the proper software in place, the reflectance of the strip can be scanned by moving the read table with the plastic and membrane laminate past the readhead.

Figure 2:
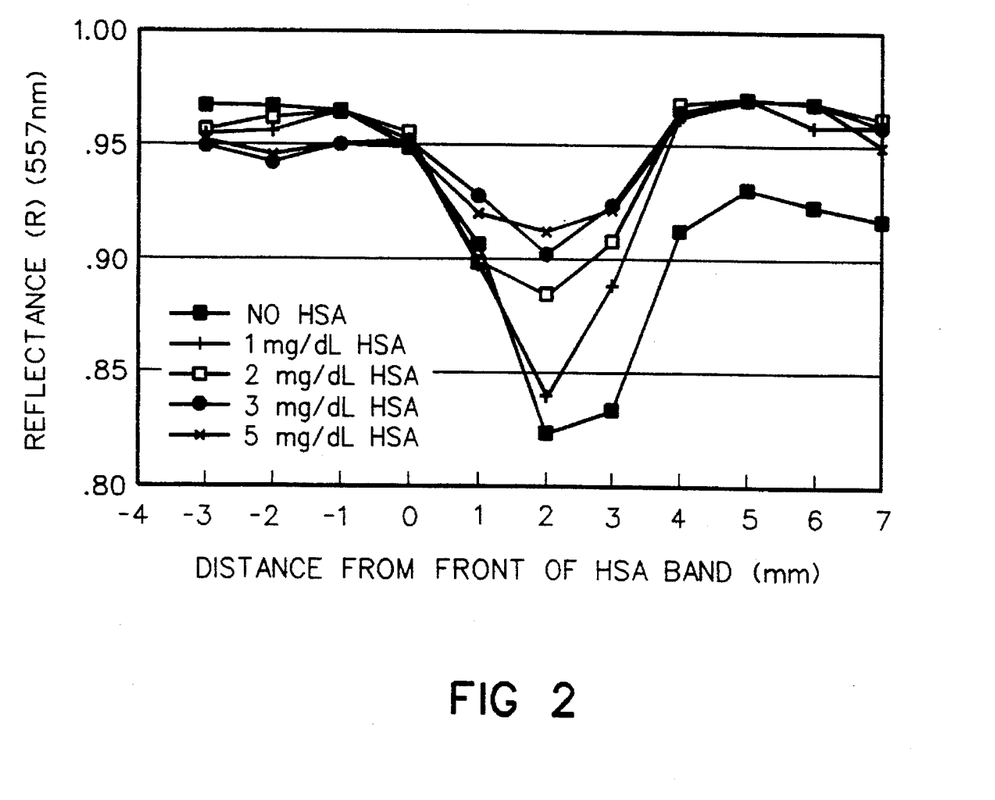
FIG. 2 is a graphic representation of results obtainable in analyzing for human serum albumin using the method of the present invention.

The results of this experiment are graphically illustrated by FIG. 2.

From FIG. 2 it can be determined that the depth of the troughs of the reflectance scans of immunochromatographic strips developed with urine samples containing various concentrations of HSA are directly proportional to HSA concentration and a dose response to HSA can be seen in reflectance. Even though the gold sol band does not cover the entire read area, the reflectance is lowered by between 10 and 15% when the band is in the read area. This 10 and 15% change in reflectance is detected even though much of the high reflectance (white) area is being measured along with the gold sol band.

If a mask with a narrow slit were added to the read-head area, the range of reflectance would be greatly increased because the high reflectance white area would not be in the read area at the same time as the gold sol band. This increased reflectance would allow better discrimination between analyte (HSA) concentrations. With the stepping motor, the spectrophotometer's strip table can be moved slowly through any area on the strip while taking consecutive readings to give good resolution for finding trough reflectances or areas in the troughs since the stepping motor can be moved a fraction of one revolution at a time.

EXAMPLE II

Quantitation of HSA in a Format Containing a Blocking Band and a Capture Zone

Figure 3:
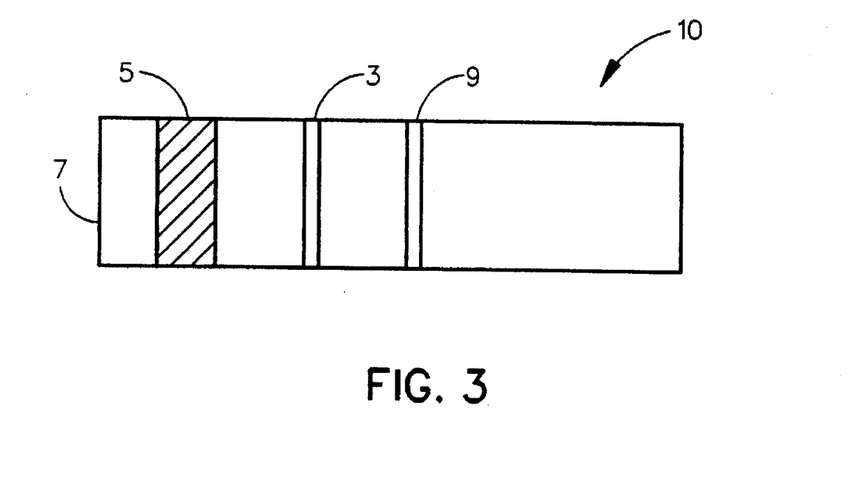
FIG. 3 represents a strip similar to that of FIG. 1 with the addition of a capture band.

An immunochromatographic strip was prepared according to the methods of Example I and the format of FIG. 3. Referring to FIG. 3, the strip 10 has a blocking band of immobilized HSA 3, a mouse anti-HSA:gold sol conjugate zone 5 and a capture band of immobilized goat anti-mouse IgG antibody 9. In preparing this band, a solution of goat anti-mouse IgG (sigma 8770) with a concentration of 5 mg/mL was prepared in 0.135M sodium chloride. This was stripped as described above at a Y distance of 4.0 cm. The stripping density was 50 µg of IgG/cm$^2$. When the sample application zone 7 is immersed in a sample containing HSA to a depth less than that needed to immerse the conjugate zone 5, fluid will flow upward from the sample by capillary action. The HSA in the sample will complex with the gold sol:anti HSA in the conjugate zone and will move up the strip along with conjugate which is free since it did not find any HSA to bind as there was a molar excess of conjugate to HSA in the sample. The free conjugate will bind the immobilized HSA in the blocking band 3 while the gold sol-anti HSA:HSA complex will continue to flow up the strip where it will be bound by the immobilized goat anti mouse IgG antibody in the capture band 9.

Figure 4A:
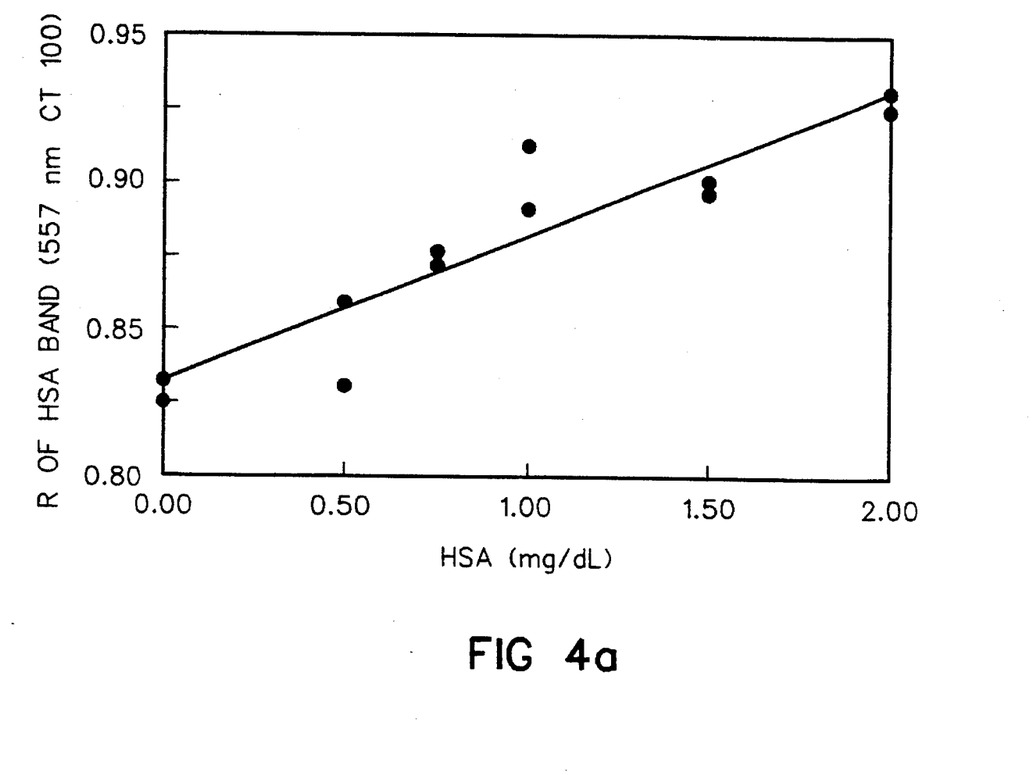
FIG. 4a is a dose response curve generated using band 3 of the strip depicted in FIG. 3.
Figure 4B:
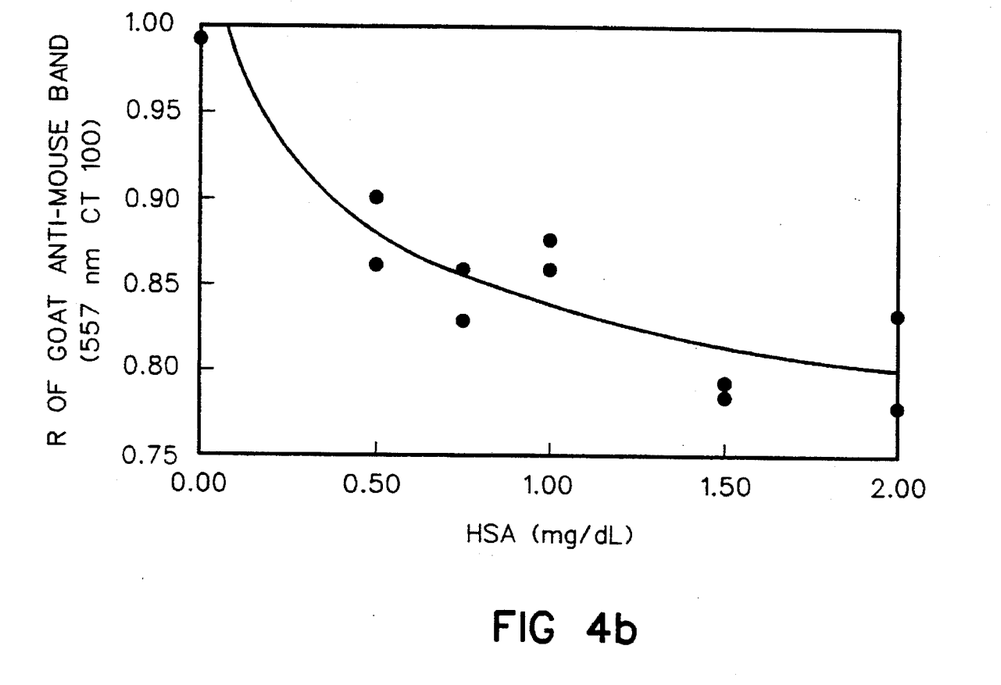
FIG. 4b is a dose response curve using band 9 of the strip depicted in FIG. 3.
Figure 4C:
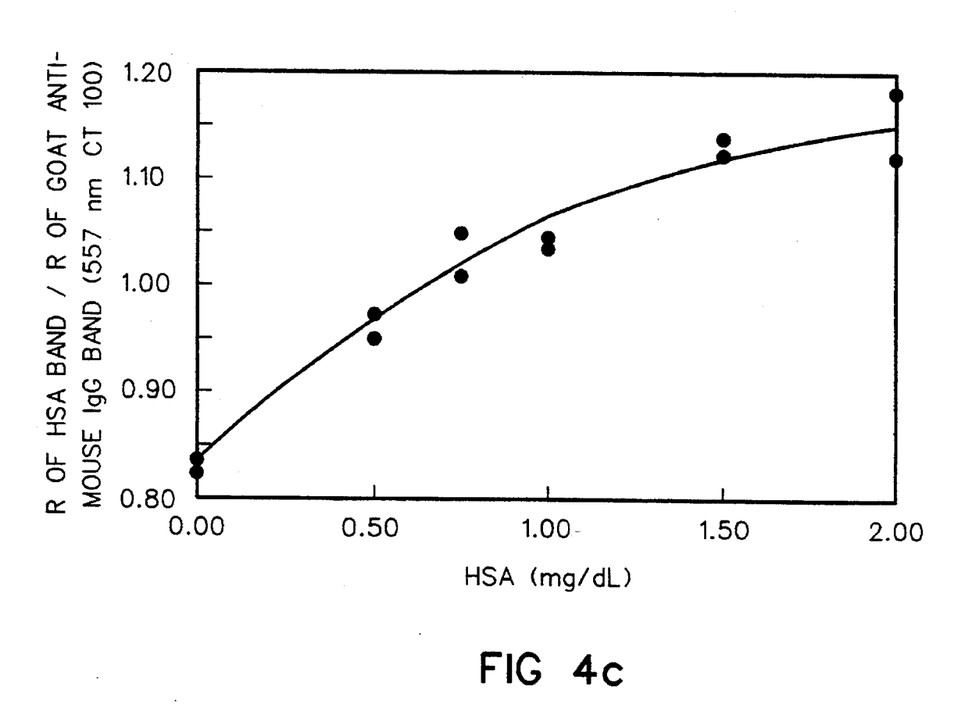
FIG. 4c is a dose response curve of the ratio of the reflectance from band 3 to that of band 9.

Strips of this format were developed with samples of medium SG urine ultrafiltrate containing concentrations of HSA of 0, 0.5, 0.8, 1.0, 1.5 and 2.0 mg/dL. Duplicate strips for each HSA concentration were run. Reflectance data at 557 nm was collected on the CT100 using a method for visually aligning the bands in the center of the 10$^{th}$ pad position. The 10$^{th}$ pad position occupies the 5 mm portion adjacent to the end of the Multistix® 10 SG urine strip product. The Multistix 10 SG product is an approximately 10.9 cm long by 5 mm wide by 0.5 mm thick piece of plastic to which 10 paper pads containing dried reagents each 5 mm by 5 mm are attached. The 10$^{th}$ pad is aligned evenly with one end of the plastic and the spacing between the pads is 2.5 mm leaving a 3.4 cm piece of the plastic at the other end which has no pads and serves as a handle area. In FIG. 4a there are plotted the results of this experiment in terms of reflectance. In this figure, in which the reflectance is from the immobilized HSA band 3 (FIG. 3), the dose response to HSA is linear in terms of reflectance (R) with two outlying values. The response of the goat anti-mouse IgG band 9 (FIG. 3) to HSA, as represented in FIG. 4b, is more scattered and-most of the reflectance drop occurred between 0 and 0.5 mg/dL HSA. However, when the reflectance value for the HSA band is ratioed to the reflectance (R) value for the goat anti-mouse IgG band the variability decreases as can be determined from FIG. 4c which plots the concentration of HSA against the ratio of reflectance of the HSA band to the reflectance of the goat anti-mouse IgG band. A curved but smooth dose response to HSA concentration is observed in FIG. 4c. This ratio can be reversed which would amount to taking the reciprocal of each ratio which would have the same effect as the ratio itself. Thus, the determination of the ratio of these two reflectance values corrects for the variability of the conjugate deposition during reagent preparation, and any unevenness in the fluid flow during the development of the strip with sample, i.e. if there is less gold sol:anti HSA on one strip than on another, the ratio of the two bands will provide a result which is corrected for the unevenness in preparation. Unevenness in fluid flow during development of the strip can be corrected for in a similar manner.

EXAMPLE III

Quantitation of HSA and IgG in a Dual Blocking Band Format

Figure 5:
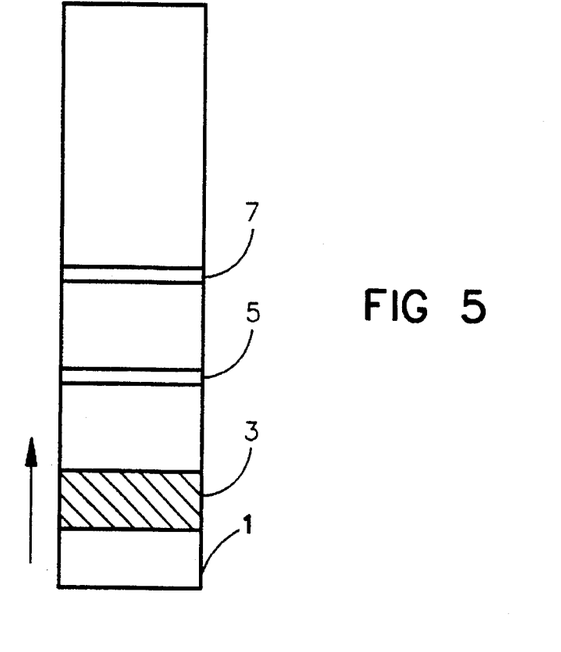
FIG. 5 represents an immunochromatographic strip containing two blocking bands 5 and 7.

Immunochromatography strips were constructed to measure both human serum albumin (HSA) and human (H) IgG in order to quantify each of these analytes independently. The strips were prepared from Immunodyne™ nylon according to the scheme of FIG. 5 to comprise a sample application zone 1 followed by a zone 3 containing gold sol labeled anti-HSA and gold sol labeled anti-(H)IgG conjugates. The strip contained two blocking bands; the first blocking band 5, containing immobilized HSA, and the second blocking band 7, containing immobilized (H) IgG.

Figure 6:
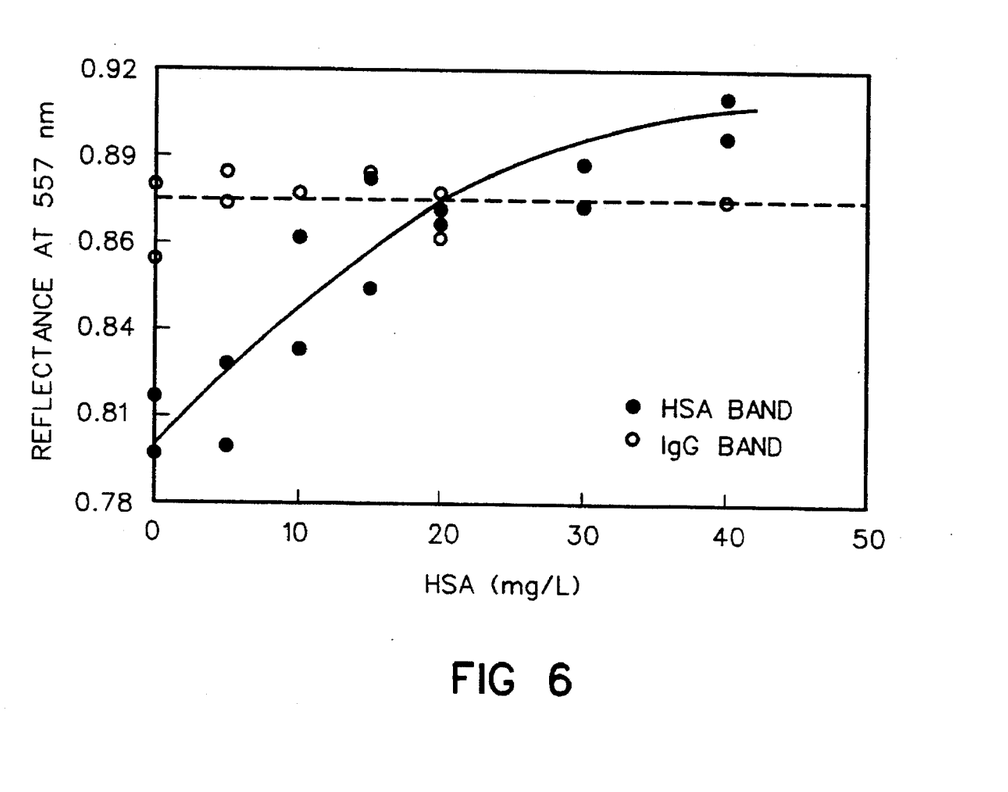
FIG. 6 is a graphical representation of the reflectance values obtained using the strip of FIG. 5 with a sample containing HSA but no IgG.
Figure 7:
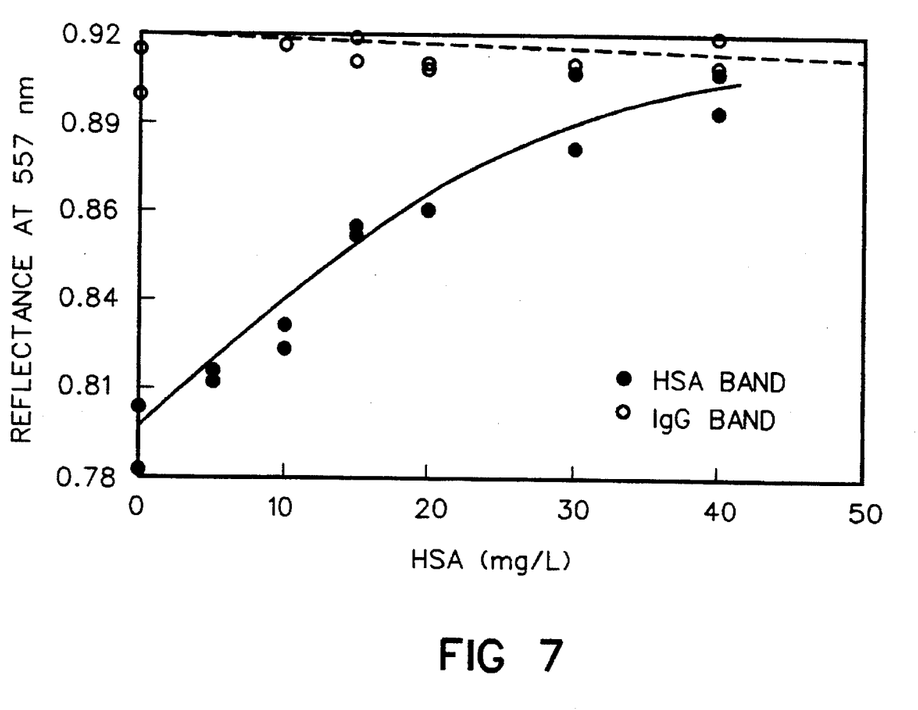

These strips were developed with test samples of an ultrafiltrate of medium SG urine containing 0, 5, 10, 15, 20, 30 and 40 mg/L HSA along with either 0 IgG or 100 mg/L (H)IgG. Two strips for each HSA concentration were examined by measuring the reflectance at 557 nm on a CT100 reflectance photometer by physically cutting and aligning the strip in the 10$^{th}$ pad position of the Multistix® SG strip to obtain reflectance readings. FIG. 6 graphically represents the reflectance for samples containing both HSA and (H)IgG blocking bands using test samples which did not contain IgG. FIG. 7 shows similar data for test samples containing 100 mg/L (H)IgG along with the various concentrations of HSA. From the data of FIG. 6 it can be determined that the reflectance of the HSA blocking band is directly proportional to the HSA concentration in the sample and the reflectance of the (H)IgG blocking band is approximately 0.88 (based on a maximum total reflectance of 1.0) due to the gold sol:anti (H)IgG which binds to it in the absence of (H)IgG in the sample. The data in FIG. 7 show the same direct proportionality of the reflectance to HSA concentration as do the data in FIG. 6, but the reflectance of the (H)IgG band is higher (0.91–0.92) due to the 100 mg/L (H)IgG in the sample. The (H)IgG binds to the gold solanti(H)IgG conjugate and will not allow it to bind to the immobilized (H)IgG in the (H)IgG blocking band. This demonstrates that the dose response to HSA is the same in the presence or absence of (H)IgG and that there is a separate dose response to (H)IgG. Accordingly, by using a strip with mixed gold sol antibody conjugates against two different analytes and in separate regions having immobilized bands of these analytes or analogs thereof, one can obtain a separate instrumentally detectable dose response to each analyte. This is important because it enables one to quantitate more than one analyte using a single immunochromatographic strip.

What is claimed is:

1. A method for determining the concentration of one or more analyte in a fluid test sample which comprises:

a) providing a test strip comprising a matrix through which the fluid test sample can flow by capillarity wherein a first region of the strip contains mobile specific binding partner for the analyte which bears a detectable label and can react with the analyte to form an analyte/labeled binding partner complex and at least one second region which contains immobilized analyte or analog thereof, b) developing the strip by applying the fluid test sample suspected of containing the analyte thereto thereby allowing the same contact the mobile, labeled specific binding partner for the analyte whereby analyte present in the fluid test sample binds to the labeled specific binding partner to form the complex leaving excess, unreacted labeled binding partner free to further react whereby the fluid test sample carries the analyte/labeled binding partner complex and unreacted labeled binding partner along the strip by capillarity to the second region containing the immobilized analyte or analog thereof in which region unreacted labeled binding partner is bound to the inmlobilized analyte in inverse relationship to the concentration of analyte in the fluid test sample, c) reading the developed strip on an instrument having a detector capable of measuring the signal from the detectable label to determine the concentration of the labeled binding partner in the second region, and d) determining the concentration of analyte in the fluid test sample by comparing the signal from the detectable label measured in step c) with the measurements of the signal made in the same manner using fluid samples containing known concentrations of analyte.

2. The method of claim 1 wherein there is a third region of the strip which contains means for immobilizing the complex formed between the analyte and the labeled binding partner and measuring the signal from the detectable label immobilized in this third region and wherein the ratio of the signal from the labeled binding partner immobilized in the second region and the immobilized complex in the third region is determined.

3. The method of claim 1 wherein the instrument contains means for moving the strip or the detector relative to each other to give accurate quantitation for regions which may not have been precisely located on the instrument.

4. The method of claim 1 wherein there are two or more mobile labeled binding partners on the strip in the same or different first regions and two or more second regions containing immobilized analytes or analogs thereof, so that two or more analytes can be determined in a single test.

5. The method of claim 1 wherein the instrument is a reflectance spectrometer.

6. The method of claim 1 wherein the matrix is comprised of a material which is capable of non-bibulous lateral flow or a bibulous material.

7. The method of claim 1 wherein the analyte is human serum albumin.

8. The method of claim 1 wherein the detectable label is a colored species.

9. The method of claim 8 wherein the colored species is a gold sol.

10. The method of claim 1 wherein the labeled binding partner is an antibody.

11. A method for quantitatively determining the concentration of one or more analyte in a fluid test sample which comprises the steps of:

a) providing a test strip comprising a matrix through which the fluid test sample can flow by capillarity said strip having a first region wherein the first region contains mobile specific binding partner for the analyte which binding partner bears a detectable label and can react with the analyte to form an analyte/labeled binding partner complex, at least one second region which contains an immobilized analyte or analog thereof and at least one third region which contains means for immobilizing the complex formed between the analyte and labeled binding partner;

b) developing the strip by applying the fluid test sample suspected of containing the analyte thereto to allow the same to contact the mobile specific binding partner whereby analyte present in the fluid test sample binds to the labeled specific binding partner to form the complex leaving excess, unreacted labeled binding partner free to further react whereby the fluid test sample carries the analyte/labeled binding partner complex and unreacted labeled binding partner along the strip by capillarity to the second region containing the immobilized analyte or analog thereof in which region unreacted labeled binding partner is bound to the immobilized analyte in inverse relationship to the concentration of the analyte in the fluid test sample and the analyte/labeled binding partner complex is carried by capillarity to the third region where it is captured by the immobilization means;

c) reading the second zone of the developed strip on an instrument having a detector capable of measuring the signal from the detectable label to determine the concentration of the labeled binding partner in the second zone and reading the third zone of the developed strip in a similar manner to determine the signal from the labeled binding partner in the third zone of the strip;

d) determining the ratio of the signal from the labeled binding partner immobilized in the second region to the signal from the labeled binding partner in the third region; and e) determining the concentration of the analyte in the fluid test sample by comparing the ratio of the signals measured in step c with the measurements of the ratios of the signals measured in the same manner for fluid samples containing known concentrations of the analyte.

12. The method of claim 11 wherein the measuring instrument is a reflectance spectrometer.

13. The method of claim 11 wherein the matrix is comprised of a material which is capable of non-bibulous lateral flow or a bibulous material.

14. The method of claim 11 wherein the analyte is human serum albumin.

15. The method of claim 11 wherein the detectable label is a gold sol.

16. The method of claim 11 wherein the labeled binding partner is an antibody.

* * * * *